US006493575B1

(12) United States Patent
Kesten et al.

(10) Patent No.: US 6,493,575 B1
(45) Date of Patent: Dec. 10, 2002

(54) FLUOROSCOPIC TRACKING ENHANCED INTRAVENTRICULAR CATHETER SYSTEM

(76) Inventors: Randy J. Kesten, 181 Ada Ave., #41, Mountain View, CA (US) 94043; Michael J. Rosinko, 1614 Husted Ave., San Jose, CA (US) 95125; Douglas R. Murphy-Chutorian, 151 Lowell Ave., Palo Alto, CA (US) 94301; Mark Roush, 19510 Manzanita Dr., Los Gatos, CA (US) 95030

( * ) Notice: Subject to any disclaimer, the term of this patent is extended or adjusted under 35 U.S.C. 154(b) by 0 days.

(21) Appl. No.: 09/326,128

(22) Filed: Jun. 4, 1999

Related U.S. Application Data

(60) Provisional application No. 60/088,018, filed on Jun. 4, 1998.

(51) Int. Cl.[7] .................................................. A61B 6/00
(52) U.S. Cl. ....................................................... 600/431
(58) Field of Search ............................... 600/374, 431, 600/585; 604/523, 532; 606/41; 607/122

(56) References Cited

U.S. PATENT DOCUMENTS

| | | | |
|---|---|---|---|
| 4,621,257 A | 11/1986 | Brown | 340/365 |
| 5,289,373 A | 2/1994 | Zarge et al. | 364/413.13 |
| 5,369,678 A | 11/1994 | Chiu et al. | 378/62 |
| 5,638,501 A | 6/1997 | Gough et al. | 395/135 |
| 5,876,373 A | 3/1999 | Giba et al. | 604/95 |
| 5,879,296 A | * 3/1999 | Ockuly et al. | 600/374 |
| 6,156,018 A | * 12/2000 | Hassett | 604/281 |

FOREIGN PATENT DOCUMENTS

| | | |
|---|---|---|
| WO | WO 96/35469 | 11/1996 |
| WO | WO 98/39045 | 9/1998 |

OTHER PUBLICATIONS

Beck, Claude S., M.D., "The Development of a New Blood Supply to the Heart by Operation," Annals of Surgery., vol. 102, No. 5, pp. 801–813, Nov., 1935.
Mirhoseini, Mahmood and Mary M. Cayton., "Lasers in Cardiothoracic Surgery," Lasers in General Surgery, Williams and Williams, pp. 216–223, 1989.
Silverman, James F., M.D. Coronary Angiography: An Introduction to Interpretation and Technique, Stanford University School of Medicine, Stanford University, 1984.

* cited by examiner

Primary Examiner—George Manuel

(57) ABSTRACT

A catheter tracking system for visualization of fluoroscopic images, the system comprising a fluoroscope for generating fluoroscopic image data, a fluoroscopic image visualization monitor, a catheter having an elongated shaft, particularly an intraventricular catheter, distal tip and a radio opaque portion adjacent the distal tip. A circumferential radio opaque band may be used to determine the relative position, orientation and motion of the catheter. An image analysis system capable of analyzing the image of the catheter and the radio opaque band, for receiving fluoroscopic image data from the fluoroscope determining physical parameters related to the left ventricle, and the relative position, orientation and motion of the catheter therein, and for determining the location and other parameters of treatment on intraventricular surfaces.

56 Claims, 10 Drawing Sheets

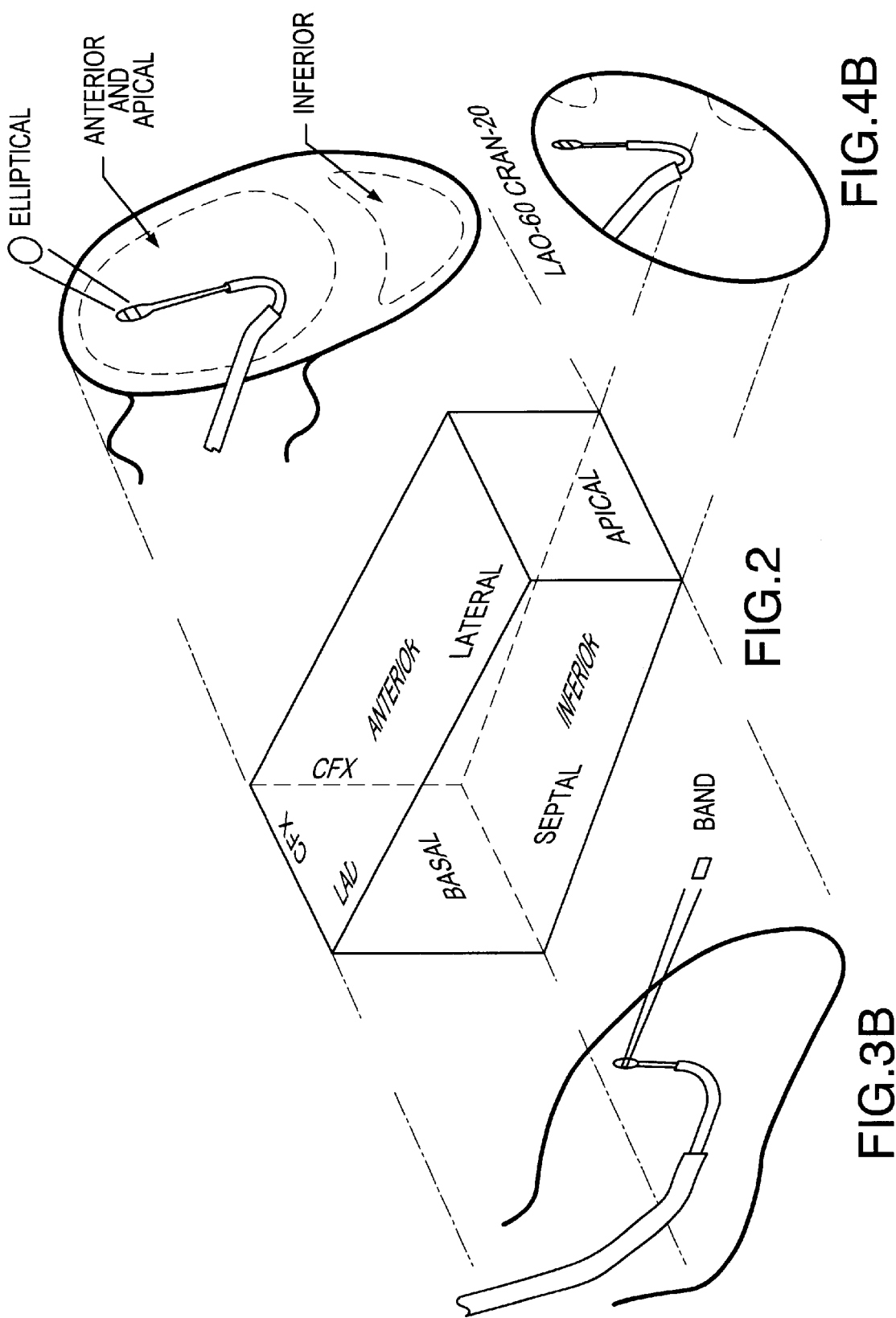

FLUOROSCOPIC TRACKING ENHANCED INTRAVENTRICULAR CATHETER SYSTEM

RELATED INVENTIONS

This Application claims the benefits of domestic priority under 35 U.S.C. 119(e) of U.S. Provisional Application No. 60/088,018 entitled "Enhanced Viewing For Myocardial Revascularization Using Computer Based Fluoroscopy Viewing", filed Jun. 4, 1998 by Murphy-Chutorian et al., which is incorporated herein in its entirety.

FIELD OF THE INVENTION

This invention relates to the field of computer based viewing hardware with fluoroscopic tools for cardiac surgery, and more particularly to viewing devices for myocardial revascularization.

BACKGROUND OF THE INVENTION

Heart disease is a significant health problem which has been the subject of substantial medical study. Bypass surgery has become commonplace; yet such surgery may be unavailable to many patients, either because of the nature of the occlusions or the physical condition of the patient. One promising alternative technique for treating such cases is known as transmyocardial revascularization (TMR). Although this technique was considered as early as the work of Dr. C. Beck "The Development of a New Blood Supply to the Heart By Operation", *Annals of Surgery*, Vol. 102, No. 5 (11/35) pp. 801–813, the method was not extensively studied until the work of Dr. M. Mirhoseini and M. Cayton, an example of which is found in "Lasers in Cardiothoracic Surgery" in *Lasers in General Surgery* (Williams and Williams; 1989) pp. 216–223.

Myocardial revascularization systems used by interventional cardiologists include a percutaneous myocardial revascularization (PMR) instrument that is a catheter and tissue removal energy delivery system that creates channels partially into the myocardium from inside the left ventricle. In the PMR procedure, an interventional cardiologist performs a cardiac catheterization procedure using a catheter with an internal optical fiber that is inserted into the femoral artery at the groin and advanced through the heart's aorta arch into the left ventricle. Once in the ventricle, the catheter is guided to the endocardium where the device creates pathways through the endocardium and partially into the myocardium.

PMR generally requires that a physician use a hand-held device that encompasses and guides either a mechanical cutting device or one or more optical fibers through which laser energy is directed. Mechanical or laser energy cuts or vaporizes heart muscle tissue immediately in front of the distal end of the device. From the standpoint of safety and efficacy, the laser based procedures minimize both ancillary tissue damage and embolic material production, both results are highly desirable. Varying penetration depths are possible. Clinical tests have demonstrated that revascularization channels/pathways, which generally communicate with the ventricle, facilitate revascularization of the heart muscle and recovery of heart function.

U.S. Pat. No. 5,876,373 entitled "Steerable Catheter", issued Mar. 2, 1999, based on application Ser. No. 08/833,352, filed Apr. 4, 1997 by Giba et al., U.S. patent application Ser. No. 09/156,963, entitled "Steerable Catheter with Tip Alignment and Surface Contact Detector", filed Sep. 18, 1998 by Khairkahan et al., and U.S. patent application Ser. No. 09/326,118, entitled "Non-deforming, Deflectable Multi-lumen Catheter" and filed Jun. 4, 1999, are incorporated herein by reference in their entirety. These applications teach steerable catheters and methods of use, particularly adapted for PMR use. The distal portion of the catheters are deflectable. Rotation of the catheters, therefore, such as within the left ventricle during a PMR procedure, will allow treatment of essentially any surface area within the ventricle. The catheters have a relative movement compensation mechanism for maintaining positioning between the distal portion of the catheter and the functional device, such as an energy delivery device disposed therein. The deflectable portion of the catheter is non-deformable.

Another approach to catheter construction for PMR is described in International Publication WO 96/35469, entitled "System for Treating or Diagnosing Heart Tissue", International Application No. PCT/US96/06700, filed May 9, 1996, to Kesten et al., and WO 98/39045, entitled "Catheter with Three Sections of Different Flexibilities", International Application No. PCT/US98/04484, filed Mar. 6, 1998, to Javier et al., are also hereby incorporated by reference in their entirety. In these systems, an aligning catheter, shaped to extend along the long axis of the left ventricle, guides a laser catheter to various and predetermined individual points within the left ventricle. The intraluminal catheter has an elongated tubular shaft with proximal, intermediate, and distal shaft sections for positioning a therapeutic or diagnostic device within a patient's body region such as a heart chamber. The intermediate shaft section has greater flexibility than the proximal or distal shaft sections, and is preferably of sufficient flexibility to easily assume the curvature of the patient's aortic arch, and reduce the force of contact between the catheter distal end and tissue defining the patient's body region to thereby reduce restriction on the rotation of the catheter. The flexible intermediate shaft section is preferably of a length to occupy a significant portion of the arctic arch, and the catheter overall length is preferably sufficient to have a catheter proximal extremity extending out of the patient and a distal extremity extending at least into an aortic passageway adjacent the patient's left ventricle. In embodiments, the distal section of a guiding or first delivery catheter, is provided with a double bend, or other predetermined geometry and dimension, to facilitate a perpendicular approach by a laser or other energy delivery device to the surface of the endocardium of the left ventricle.

Fluoroscopy is used in PMR and other intracardiac catheter-based procedures for guidance and visual marking, to locate the optical fiber's distal end inside the heart for proper channel formation and prevent excessive penetration thereof into the myocardium. A plastic transparency may be placed on the fluoroscope monitor, the shape of the ventricle manually traced using an ink marker, and then manually marking the channels as they are formed. The manual markings are often not drawn on the transparency exactly where the interventional cardiologist, having a slightly different optical vantage point of the procedure, might see the references, thereby increasing the complexity of the positioning the catheter and estimating the precise position inside the left ventricle to form channels. Furthermore, manually drawing an outline of the left ventricle based on a fluoroscopic image, which is moving according to the cardiac or respiratory cycles, can be problematic. Additionally, dye typically injected to enhance the fluoroscopic image has a short duration. Moreover, since most current fluoroscopy imaging systems are two-dimensional based imaging systems, the cardiologist must monitor two perpendicular planar images of a heart to view a PMR's optical fiber's position in a three-dimensional perspective by switching between two images. Furthermore, tracking already created channels is a problem since the screen may not readily show locations of these previously created channels. Additionally, excessive radiation while using a fluoroscope system poses radiation hazards to patient and operating room personnel.

U.S. Pat. No. 5,369,678 entitled "Method for tracking a catheter probe during a fluoroscopic procedure," by Chiu, teaches of fluoroscopy for monitoring the location of a catheter inside a body during balloon angioplasty or laser ablation for percutaneous interventional procedures. Chiu teaches a method for determining catheter tip location from fluoroscopic images using digital imaging processing techniques that confine full X-ray dosage to a central area, compensating for the reduced X-ray dosage in the peripheral areas by computer imaging enhancement but does not solve the problems currently associated with the use of fluoroscopy for guidance and visual marking in PMR and other intracardiac catheter-based procedures.

It is desirable to have apparatus and methods that use integrated hardware of a computer workstation, video capture, image display and manipulation and angular feedback from the fluoroscopy device to assist the cardiologist during the PMR procedure. There is a further need for apparatus and method that solves the problems associated with the use of fluoroscopy for guidance and visual marking in PMR and other intracardiac catheter-based procedures. Furthermore, there is a need to reduce the complexity of positioning such catheters and estimating the precise position inside the left ventricle to form channels during myocardial revascularization.

SUMMARY AND ADVANTAGES OF THE INVENTION

This invention describes a method of using computer based image processing techniques to automate this process as well as adding new capabilities to allow faster and more accurate placement of channels. An advantage of the disclosed invention is to solve the problem of determining catheter location within the left ventricle.

It is a further advantage to replace the current manual channel mapping technique with a computerized, video-based map. The computer-based channel map would also have greater accuracy than the manual map.

The present invention is a method to use fluroscopic image processing preferably in combination with specifically designed radio opaque markers on the distal portion of an intraventricular catheter to provide accurate information regarding the location and orientation of the catheter. This would be a useful enhancement to the PMR procedure. The distal portion of the intraventricular catheter is marked with asymmetric markers that are spaced a known distance apart on at least two portions of the catheter that are roughly orthogonal to each other, or at least or on two portions of the catheter that have a known angle between them.

The fluoroscopic image is processed using image-processing techniques that use edge-detection and pattern recognition to determine the 2-D location of these markers. The software then compares the 2-D geometry to the known spatial relations of the various markers and derives the true 3-dimensional location and orientation of the catheter. This invention provides additional accurate information regarding catheter position and orientation without requiring any imaging modalities other than fluoroscopy, which is already in use for these procedures. The combination of specifically designed system of markers, which may be radially asymmetric in order to provide information regarding rotational orientation, with edge-detection and pattern-recognition software provides location and orientation information for a catheter used in intraventricular procedures.

It is a further advantage of the present invention to decrease the degree to which the fluoroscopy related PMR procedure is dependent upon orthogonal visualization capability or means, thus allowing the user to remain predominantly in an RAO-30 projection throughout most of the procedure Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2 is a representative orthogonal drawing of the left ventricle portion of the human heart of the system of the present invention.

FIG. 3B is a representative RAO-30 projection view of an intraventricular device within the left ventricle of the system of the present invention.

FIG. 4B is a representative LAO-60 projection view of an intraventricular device within the left ventricle of the system of the present invention.

DETAILED DESCRIPTION OF THE INVENTION

Figure 1:
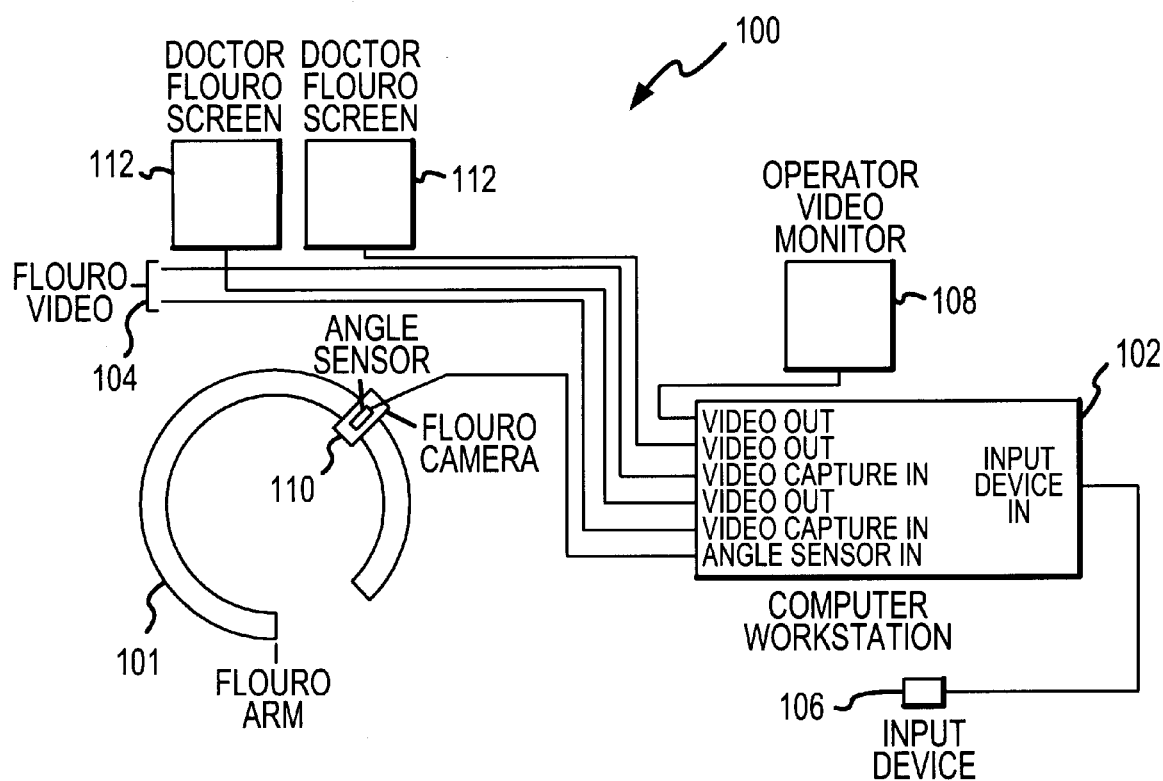
FIG. 1 is a representative schematic drawing of the fluoroscopic tracking enhanced intraventricular catheter system including fluoroscope interface with computer workstation and distributed viewing monitors.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

Input Device

Fluoroscopy is used in PMR to locate the optical fiber inside the heart for proper channel formation and the invention herein provides an apparatus and method using a computer, video capture, image display and manipulation and angular feedback from the fluoroscopy system. Using a dye enhanced image of a patient's heart, the workstation captures the image by a video capture device which is part of the workstation. In a preferred embodiment of the present invention, the major features in this heart image, such as walls and arteries, are outlined using a graphical input device 106, such as a light pen or mouse. This heart image is then over-layed on top of the real-time fluoroscopic image shown on a doctor's fluoroscopic image monitor 112 during the PMR procedure, thus providing the cardiologist information of location of the PMR device's optical fiber within the heart.

FIG. 1 is a representative schematic drawing of the catheter system 100 of the present invention including fluoroscope interface with computer workstation and distributed viewing monitors. The apparatus includes a fluoroscope 101 and computer workstation 102 with at least two channels 104 of video capture capability. A graphical input pointing device 106, such as a mouse or light pen, local and remote video screens 108 and an angle sensor and input device 110 for determining fluoroscope angle are also included.

The instant invention's workstation 102 can include the hardware as taught in Zarge et al.'s U.S. Pat. No. 5,289,373 entitled "Method and Apparatus for Real-Time Tracking of Catheter Guide Wires in Fluoroscopic Images During Interventional Radiological Procedures," which is incorporated by reference in its entirety. Zarge et al. teach an apparatus for real-time tracking of a catheter guide wire for a catheter in a patient undergoing an interventional radiological procedure. The apparatus includes an image processing unit for processing digitized fluoroscopic images from a fluoroscope image output. The image processor uses an algorithm for locating the image of the catheter in the fluoroscopic image. The image processor creates a two-dimensional model of the catheter for dynamic display on an operating room live image video monitor. The instant invention further incorporates a dual image capture feature to allow for the two normal plane views of the heart.

Figure 3A:
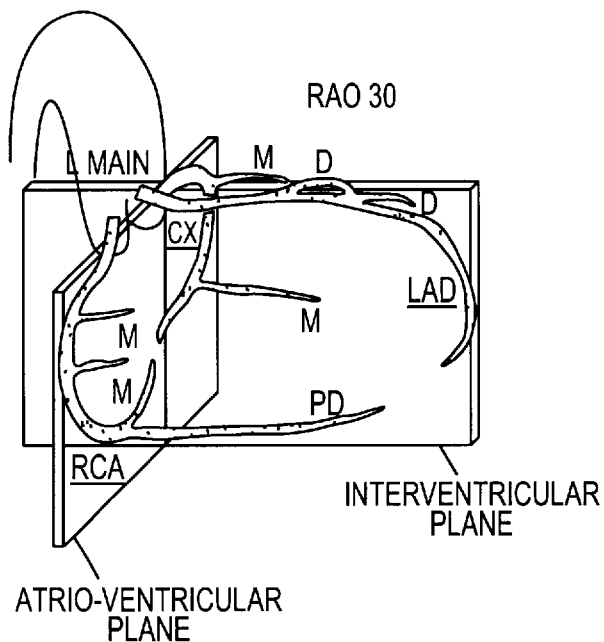
FIG. 3A is a representative RAO-30 projection view of the entire heart as obtained in the system of the present invention.
Figure 4A:
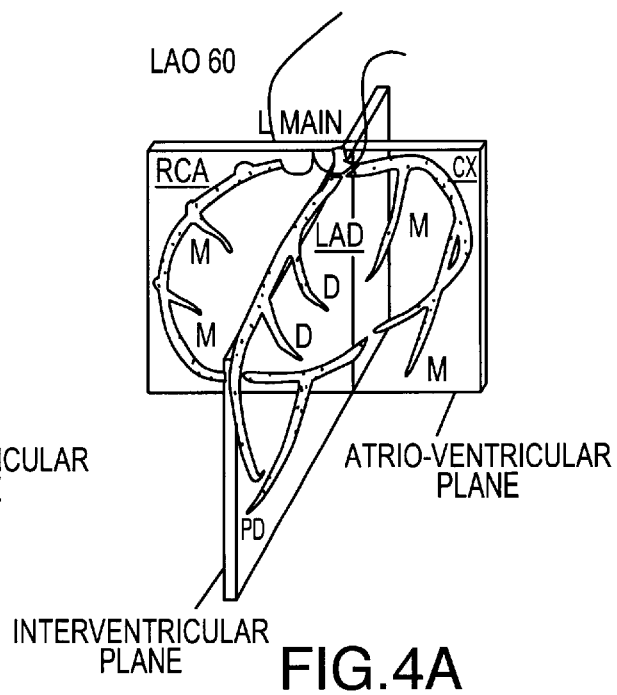
FIG. 4A is a representative LAO-60 projection view of the entire heart as obtained in the system of the present invention.

When used in conjunction with a single or bi-plane fluoroscopy unit, the system supplements the monitor or monitors provided with the fluoroscope system that are used for live images with one or more, typically two, video screens used to map the progress of the therapeutic procedure by superimposing one or more of the elements described in (1) onto either a still frame fluoroscopic image previously acquired or onto the live fluoroscopic image. The system can have a "last image hold" function on each screen, so that the user can simultaneously compare the appearance seen from one of the fluoroscopic projections, such as RAO-30 (FIG. 3A), with the appearance seen from an orthogonal projection, such as LAO-60 (FIG. 4A). This feature will allow the user to more quickly and more accurately determine the true location of the catheter within the three-dimensional heart cavity by "combining" the image of the specifically designed radiopaque elements of the catheter, such as the cylindrical distal lens marker, and to compare that location with on-screen markings that indicate previous treatment sites, thus avoiding a second treatment at the same location. Note that in a single-plane setting, these two views would by necessity be acquired at different points in time, since the X-ray tube and image-intensifier will need to be rotated from RAO to LAO. The invention allows the user to simultaneously "combine" these two images and assess a true catheter position as well as compare current catheter position to previous treatment sites. Thus, when used in a single-plane catheter lab, the invention would allow for the storing of a still fluoroscopic image acquired with the fluoroscope in a given projection while allowing the continuous full-motion display of the live fluoroscopic image from a different projection. An extension of this invention is to store not a still image of a single video frame but a loop of some duration showing full motion.

An Image Analysis System (IAS) replaces some or all of the functionalities attributed to the light-pen or touch-screen as input devices. The IAS contains edge-detection, motion detection and other image-analysis algorithms to, for example, automatically determine the ventricular outline following a contrast injection in fluroscopic acquisition of a left-ventricular angiogram ("ventriculogram"). In this case, the user initiates the "Ventriculogram Mode" by depressing a switch on the console of the IAS and then immediately performing the injection. Following this the LAS would use edge-detection algorithms to determine and then trace the ventricular outline. Algorithms may also be used that do not require the user to indicate a point within the outline prior to the edge detection. This "tracing" function would be provided for both of the orthogonal views used.

As PMR channels are created, the workstation operator marks them on a video overlay 108, again using the graphical input device 106, thus providing a channel mapping of created channels and avoiding a repeated treatment at the same tissue site. The inputting device 106 can be a light pen using well known hardware for this procedure or a touch CRT screen as taught by Brown et al., U.S. Pat. No. 4,621,257 entitled "Video Display Touch Detection Digitizer," which is incorporated by reference in its entirety. Brown et al. teach a video display touch detection digitizer for generating the coordinate position when the video display is touched. The light signals for the X and Y coordinate array are generated from the raster scan signals of the video display during selected periods of the vertical and horizontal blanking intervals. Vertical and horizontal mirrors reflect, respectively, the resulting row and columns of light signals across the screen of the video display where other mirrors reflect the signals to, respectively, row and column signal detectors. Control circuitry detects the resulting interruption in the rows and columns of light signals when the screen of the video display is touched and generates signals representing the touch coordinates.

In two-dimensional fluoroscopic imaging used to guide the catheter for PMR channel formation, a third-dimension is located by rotating the fluoroscopic image perpendicularly to check fiber location. Once treatment sites are established, the normal view is restored and a line of channels is formed. The fluoroscope is then rotated perpendicularly again, the fiber is moved to a new site, and the fluoroscope is brought back to the original position again and another row is formed. This procedure is repeated until treatment is completed. The channel mapping described earlier is only two-dimensional. Consecutive rows of channels may not appear to be spatially separated. If the fluoroscopic image is captured during the perpendicular check of fiber position, and the fiber position is marked on a captured image of this position, and the fluoroscope angle is captured, a pseudo three dimensional map of channel formation can be constructed. This prevents the possibility of a row of channels being overlayed.

The workstation cardiologist using the pointing device performs all operations. The dye enhanced image is first captured. The operator then outlines walls and arteries with the input pointing device. This image is then overlayed onto the live fluoroscope video screen output for visual feedback. As channels are formed in each row, the cardiologist marks them graphically on the overlay with the input pointing device. Each time the fluoroscope is rotated perpendicular to move the fiber to the next row position, the image is captured. The operator marks the fiber position with the input device, captures the fluoroscope angle, and overlays this onto a second video monitor which is visually displayed, Thus, the cardiologist uses one video monitor to see and track two-dimensional channel formation for each row and the second video output monitor to visualize and track row location in the third dimension. A virtual three-dimensional image on the second screen can be outputted as well since fluoroscope angle and fiber position are known.

The images for overlaying the live fluoroscope video screen output for the cardiologist visual feedback can be implemented by using the teaching of Gough et al., U.S. Pat. No. 5,638,501, entitled "Method and Apparatus for Displaying an Overlay Image," which is incorporated by reference in its entirety. Gough et al. teach a method and apparatus for providing a translucent overlay image over a base image on the screen of a computer system. The method of Gough et al includes steps for running an application program on a central processing unit (CPU) of a pen computer system to produce a base image in a screen coupled to the CPU; and running an overlay program on the CPU to produce an overlay image on the screen such that portions of the base image which are overlapped by the overlay image are at least partially visible through the overlay image. The overlay program is a computer implemented process comprising the steps of displaying an overlay image on the screen, intercepting screen inputs which contact the overlay image, processing the intercepted screen inputs in the CPU, and updating the application program based on the processed screen inputs. In addition, a pen computer system includes a central processing unit (CPU), a screen assembly coupled to the CPU, a mechanism coupled to the screen assembly for displaying a base image on the screen assembly, and a mechanism coupled to the screen assembly for displaying an overlay image on the screen assembly such that portions of the base image which are overlapped by the overlay image are at least partially visible through the overlay image. The screen assembly includes a tablet mechanism coupled to the CPU which can receive input from a pen or stylus. The mechanism for displaying a base image includes a first computer implemented process running on the CPU which produces first video data and a video driver circuit coupled between the CPU and the screen assembly. The mechanism for displaying the overlay image includes a second computer implemented process running on the CPU to produce second video data, and a video driver circuit coupled between the CPU and the screen assembly. There is also a mechanism for blending the first video data and the second video data to produce a blended image on the screen assembly. This blending mechanism can include the second computer implemented process, or can comprise the video driver circuitry. The instant invention would use a dual based system comparable to the above described system and the coordinated actions by the operator would provide the basis for three-dimensional input.

RAO-30 and LAO-60

FIG. 2 shows a representative orthogonal drawing of the left ventricle portion of the human heart of the system of the present invention. "Coronary Angiography" by James F. Silverman, M.D., provides an introduction to interpretation and technique of fluoroscopic imaging related to the heart and coronary arteries. The right anterior oblique or RAO projection, such as at an angle of 30 degrees from center (RAO-30), provides a "long-axis" or "side" view of the left ventricle. FIG. 3A is a representative RAO-30 projection view of the entire heart as obtained in the system of the present invention. FIG. 3B is a representative RAO-30 projection view of an intraventricular device within the left ventricle of the system of the present invention. When an intraventricular catheter is positioned within the left ventricle, such that it aligns with the long axis, it will be seen extending across the left ventricle from the base on the left of the view to the apex of the left ventricle on the right. A coaxial catheter system as taught by Kesten et al., includes an outer aligning catheter with shaped tip, to align an inner delivery or laser catheter with a shaped tip, with the long axis of the left ventricle. The fluoroscopic image of the RAO view shows the shaped tip of the aligning catheter with no foreshortening. The distal portion of the laser catheter shaft that is proximal to its shaped distal tip will be seen extending outward from the aligning catheter tip toward the apex of the left ventricle. However, the rotational orientation of the distal shaped tip of the laser catheter, and thus the region that the catheter is targeting, is not shown.

Information can also be obtained in the orthogonal left anterior oblique projection or LAO, typically LAO-60, by rotating the position of the fluoroscope about 90 degrees.

FIG. 4A is a representative LAO-60 projection view of the entire heart as obtained in the system of the present invention. FIG. 4B is a representative LAO-60 projection view of an intraventricular device within the left ventricle of the system of the present invention. The LAO view provides a "short-axis" view of the left ventricle wherein the shaped tip of the aligning catheter is seen with complete foreshortening and appears to be straight or nearly straight. The rotational orientation of the shaped distal tip of the laser catheter clearly shows the region that would be targeted if the tip of the device were brought into endocardial contact. Using a clock face analogy, the LAO view shows the anterior region from about 11:00 to 2:00, the lateral region from 2:00 to 5:00, the inferior region from 5:00 to 8:00 and the septal region from 8:00 to 11:00. Again, however, this method requires moving the fluoroscope into a second position for visualization of the size, shape and position of the left ventricle, which is time-consuming and interrupts not only the procedure, but can also result in loss of orientation by the interventional cardiologist performing the procedure.

Image Analysis

Figure 5A:
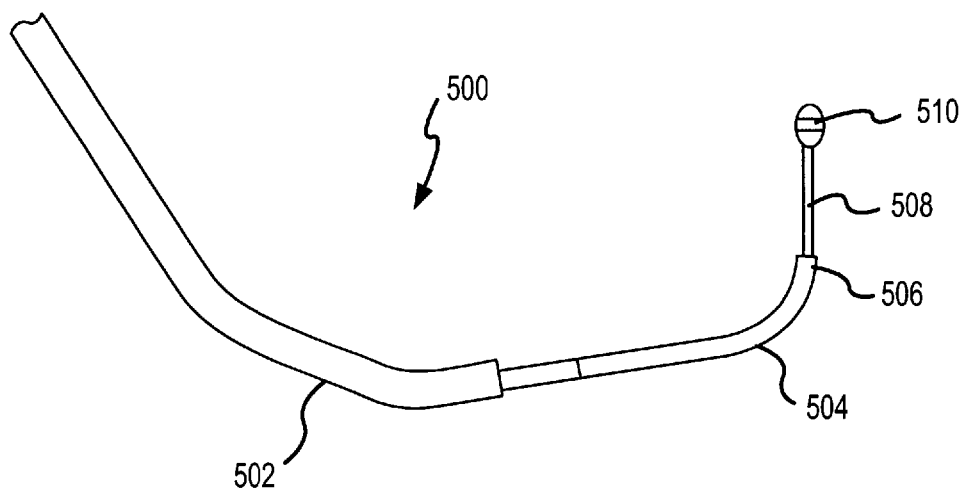
FIG. 5A is a representative elevation view of a typical catheter used in the system of the present invention.

FIG. 5A is a representative elevation view of a PMR catheter 500 for use in the system of the present invention and includes an aligning catheter 502, an energy delivery catheter shaft 504 with preformed distal tip 506, and an energy delivery device or waveguide 508, such as an optical fiber or fiber bundle, with associated radio opaque tip marker 510 at a distal end of the delivern device 508. Radio opaque markers can be disposed at any predetermined point on the catheter 500, typically at points on the aligning catheter 502, the delivery device catheter shaft 504 or the delivery device 508.

Radio Opaque Markers

U.S. patent application Ser. No. 09/107,843 entitled "Intracorporeal Device with Radiopaque Marker", Rosenthal et al., filed Jun. 30, 1998, is herein incorporated by reference in its entirety. This application teaches a catheter with an elongated shaft having an asymmetric radio opaque marker disposed upon or within the distal end thereof. The radio opaque marker member enables the user to grossly distinguish orientation of the distal end of the device under fluoroscopic and similar imaging techniques. This offers a significant benefit in the time saved by not having to rotate the fluoroscope to an LAO projection. The delivery catheter system is configured in some embodiments to deliver an elongated diagnostic or therapeutic device to a desired location within a patient's heart.

In a preferred embodiment of the present invention, the distal portion of the intraventricular catheter is marked with asymmetric markers, which may be radially asymmetric, that are spaced a known distance apart on at least two portions of the catheter that are roughly orthogonal to each other, or at least on two portions of the catheter that have a known angle between them. The fluoroscopic image is processed using image-processing techniques that use edge-detection and pattern recognition to determine the 2-D location of these markers. The software then compares the 2-D geometry to the known spatial relations of the various markers and derives the true 3-dimensional location and orientation of the distal portion of the catheter.

Although a radiopaque marker preferably is used at the catheter tip to allow for aspect perspective, no specific design of radiopaque marker is preferred as long as the IAS is "informed" as to the dimensions and radiopaque appearance. The particular design aspects of the markers, on the other hand, are directed to gaining from a single view some or all of the information that might have been obtained from a pair of orthogonal views. This is accomplished first by using radiopaque elements designed to present additional information regarding catheter position and orientation when viewed from a single fluoroscopic projection, and then by combining such radiopaque elements with an Image Analysis System.

In another embodiment, the radio opaque markers may be a series of evenly spaced radio opaque markers placed at the distal portion of the catheter. This approach is particularly useful when a tip-deflectable catheter, such as described above, is used. Evenly spaced marker bands provide non-ambiguous information regarding catheter rotation as opposed to catheter deflection. For example, if the catheter is oriented toward the anterior wall and is then straightened (i.e. the tip deflection is reduced), the appearance of the catheter tip in the RAO projection would be ambiguously similar to that as would be seen had the catheter been rotated toward the lateral wall but not straightened. If a series of evenly space markers are present however, the two situations are easily distinguished. In the first instance the catheter tip will appear more straight and the distance between markers is maintained, and in the second instance the catheter tip will appear more straight but the distance between markers will be reduced due to foreshortening.

Figure 5B:
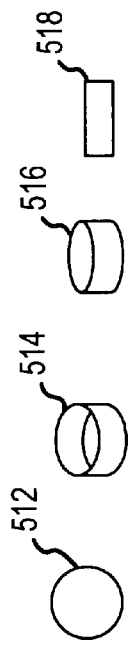
FIG. 5B are representative top, orthogonal and elevation views of a typical radio opaque marker band for use on the distal tip of a typical catheter of the present invention.

FIG. 5B are representative top, orthogonal and elevation views of a typical radio opaque marker band for use on the distal tip of catheter 500 of the present invention. It will be understood, based on the foregoing, that the radio opaque marker band 510 will appear as a perfectly round, hollow, band with a circular shape 512 when viewed from directly above or below. The band 510 will appear as an elliptical band 514 when viewed at an angle to the marker 510. The band 510 will also appear elliptical on the upper and lower edges but will not have any open, elliptical internal space, as seen in 516, when viewed at an angle approaching the elevation or side view. Finally, when the view is directly from the side, the marker 510 will appear as an essentially perfectly rectangular stripe 518.

Figure 5C:
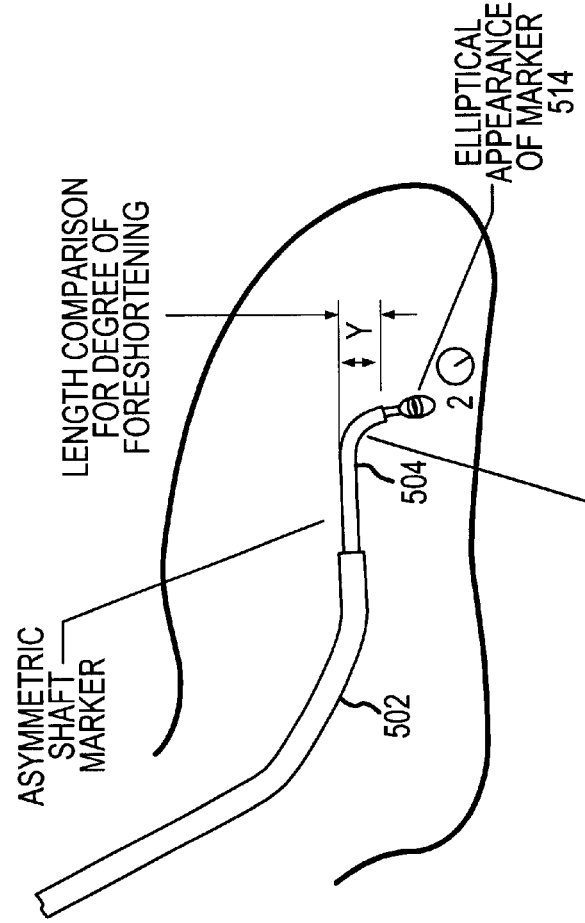
FIG. 5C is a representative RAO-30 projection view of an intraventricular catheter in the left ventricle of the present invention.

FIG. 5C is a representative RAO-30 projection view of an intraventricular catheter in the left ventricle. As described above, the catheter comprises an aligning catheter 502, through and out of which an energy delivery catheter 504 is extendable. Since the energy delivery catheter is curved, or deflectable, the foreshortening parameter X can be measured optically. It will also be apparent to those skilled in the art that the length of the foreshortening parameter X can also be measured by an image-analysis system. Based on the known or predetermined curvature of the energy delivery catheter 504, the foreshortening parameter X will indicate the degree of angular orientation of the catheter 500. As shown in FIG. 5C, since the catheter is oriented so as to direct the distal tip of the catheter 502 parallel to the plane of the projection, in this case an RAO-30 view, the foreshortening parameter X indicates that there is no foreshortening. X will have its greatest value, i.e., its greatest length, since the distal tip of the wave guide 508 is deflected within, or parallel to, the plane of the projection. The orthogonal is not viewed directly. However, as shown, a miniature "clock face" 1 reveals the orientation of the distal tip of the catheter 500 as would be viewed in an orthogonal view of the ventricle, such as in the LAO-60 view. In this manner, although only one view is shown on a monitor, the orthogonal view is represented by a small "clock face" 1 which, in a preferred embodiment, is generated by an image-analysis system. The miniature "clock face" 1 can also be created manually, based on knowledge of a predetermined, initial, visualized or calculated orientation of the catheter 500 in the left ventricle.

In this embodiment, the "clock face" 1 indicates that the catheter is orientated to treat an inferior wall. The "hand" of the "clock face" is shown pointed directly downward, in a 6 o'clock position, toward an inferior wall surface. Additionally, the fluoroscopic image of the radio opaque marker 510 appears to be a rectangular stripe 518 as shown in FIG. 5B.

Figure 5D:
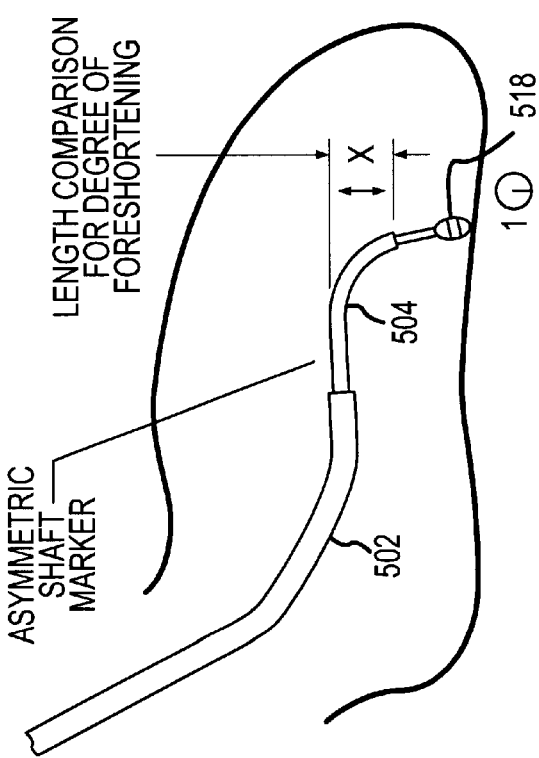
FIG. 5D is another representative RAO-30 projection view of an intraventricular catheter in the left ventricle of the present invention.

FIG. 5D is another representative RAO-30 projection view of an intraventricular catheter 500 in the left ventricle of the present invention. In this view, the foreshortening parameter Y will correspond to a length of wave guide, which appears somewhat shorter than indicated by parameter X. An image-analysis system can generate another image of the "clock face". In this case, the "clock face" 2 indicates that the catheter is orientated to treat an inferolateral wall. The difference in length between foreshortening parameter X and foreshortening parameter Y indicates the degree which the angular orientation of the catheter 500 has been changed. Additionally, the "clock face" 2 indicates that the catheter 500 has been rotated angularly to the back, or out of the plane of the image of FIG. 5C and FIG. 5D. As shown, the "clock face" 2 indicates a single hand pointing to about a 4 o'clock or 5 o'clock position. It will be apparent that the "clock face" 2 can be created based on the measured difference between the foreshortening parameters X and Y. This can be done by an image-analysis system also. Thus, it is apparent that the orthogonal projection of the catheter 500 shown in FIG. 5D would indicate that the energy delivery device is pointed toward an inferolateral wall surface, such as at an angle corresponding to the 4:00 or 5:00 positions, as opposed to the inferior wall directly, as shown in FIG. 5C. The degree of foreshortening, therefore, can be used to indicate the degree of angular rotation of the catheter 500. A second LAO-60 view is not needed when the RAO-30 view is combined with the foreshortening parameter calculation to determine the actual orientation of the distal tip of the catheter 500. Thus, the fluoroscopic image of the radio opaque marker 510 appears to be elliptical 514 as shown in FIG. 5B, another indication of the angular rotation of the catheter 500.

Figure 5G:
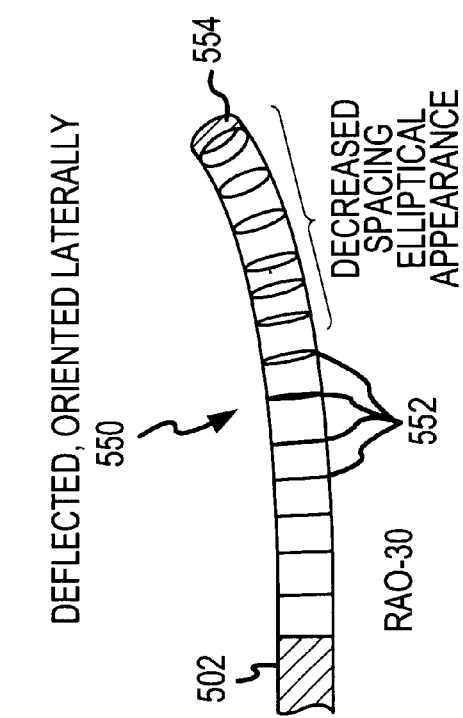
FIG. 5G is a representative elevation view of the partially deflected, laterally oriented distal end of an intraventricular catheter with set of evenly spaced band-like radio opaque markers of the of the present invention shown in FIG. 5E.
Figure 5E:
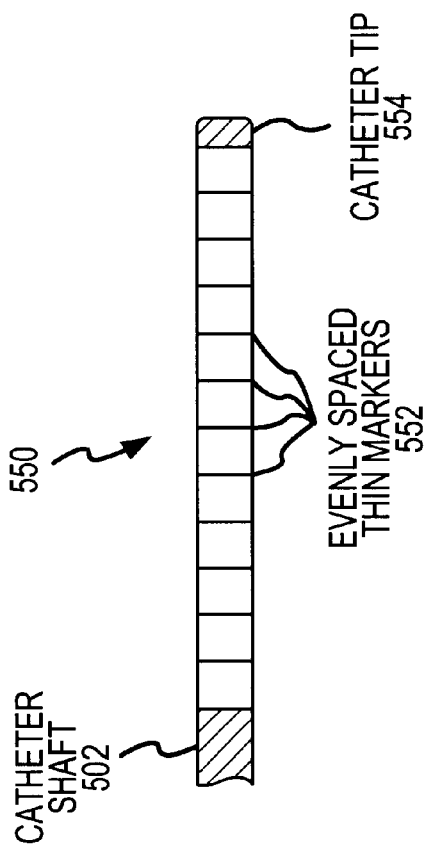
FIG. 5E is a representative elevation view of the distal end of an intraventricular catheter with a set of evenly spaced band-like radio opaque markers of the present invention.
Figure 5F:
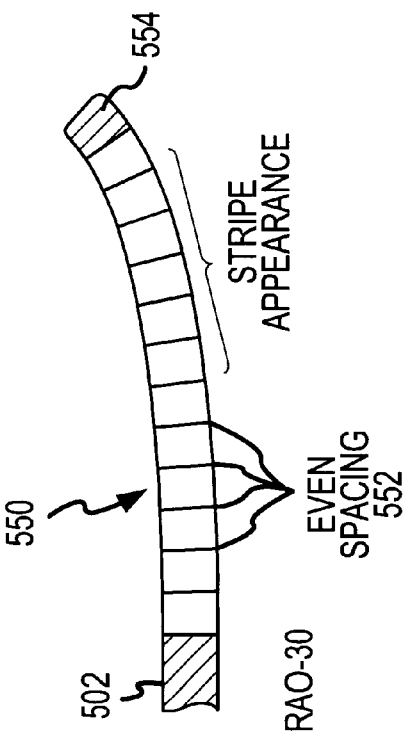
FIG. 5F is a representative elevation view of the partially deflected, apically oriented distal end of an intraventricular catheter with set of evenly spaced bandlike radio opaque markers of the of the present invention shown in FIG. 5E.

FIG. 5E is a representative elevation view of the distal end 550 of an intraventricular catheter with a set of evenly spaced band-like radio opaque markers 552 of the present invention. FIG. 5F is a representative elevation view of the partially deflected, apically oriented distal end 550 of an intraventricular catheter with set of evenly spaced band-like radio opaque markers 552 of the of the present invention shown in FIG. 5E. FIG. 5G is a representative elevation view of the partially deflect, oriented distal end 550 of an intraventricular catheter with set of evenly spaced band-like radio opaque markers 552 of the of the present invention shown in FIG. 5E.

The evenly spaced radio opaque bands or markers 552 appear as stripes in FIG. 5F. In this case, the stripe-like appearance of the markers 552 will indicate to the surgeon, and also will be recognizable in a fluoroscopic optical analysis, as an indication that the distal tip 550 of the catheter is oriented in a plane perpendicular to the line of sight of the fluoroscope. However, when the distal end 550 is directed laterally as shown in FIG. 5G, the markers 552 appear and are recognizable as elliptical. Moreover, the degree of ellipticity, coupled with knowledge of the direction of rotation of the catheter within the ventricle provides complete spatial information characteristic of the position, motion and treatment by an interventional catheter.

It will be understood that contemplating the use of deflectable and shaped aligning and delivery catheters, fiber optic equipment, visualization and treatment apparatus, adding to, decreasing, diminishing the radiopacity of the varying sections of the systems will provide for enhanced visualization, recognition and control. Thus, when the tip of a catheter is rotated towards the septal or lateral walls while being viewed in an RAO projection, it will be understood that the physical amount of material present between the x-ray tube and the image intensifier of the fluoroscope will be increased and a fluoroscopic image thereof will appear increasingly opaque, i.e., the change in opacity can be correlated with degree of rotation as well as the position of the tip and other portions.

Altering the distal catheter tip such that it is essentially a thin walled cylindrical portion or cylinder will have a band like appearance when oriented anterior or inferior. The same type of cylindrical tip will have a circular appearance when deflected laterally or septally.

Figure 5H:
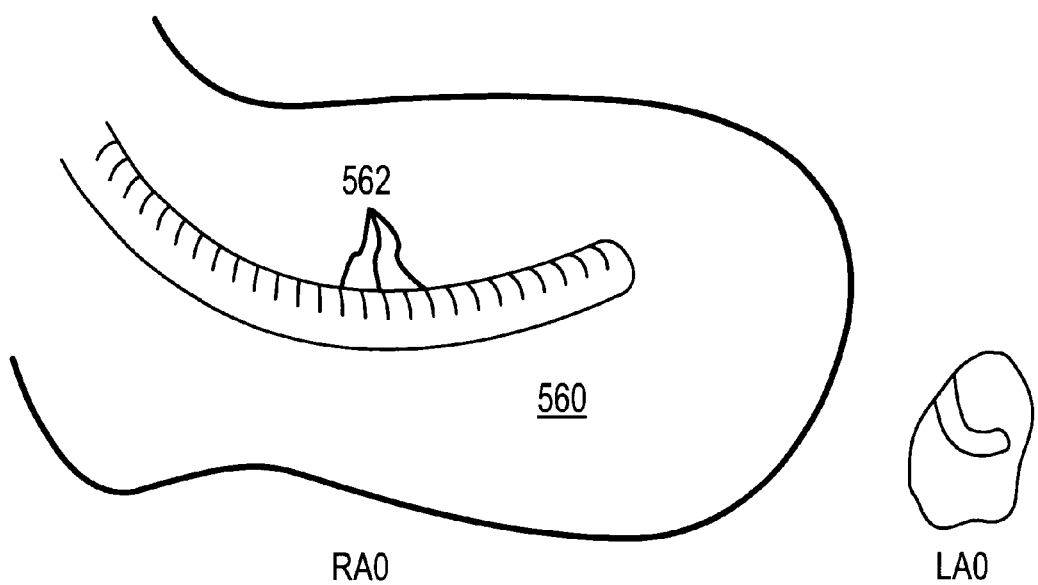
FIG. 5H is a representative RAO and LAO projection view of the distal end of an intraventricular catheter in the left ventricle with set of radially asymmetrically spaced radio opaque markers of the present invention.
Figure 5I:
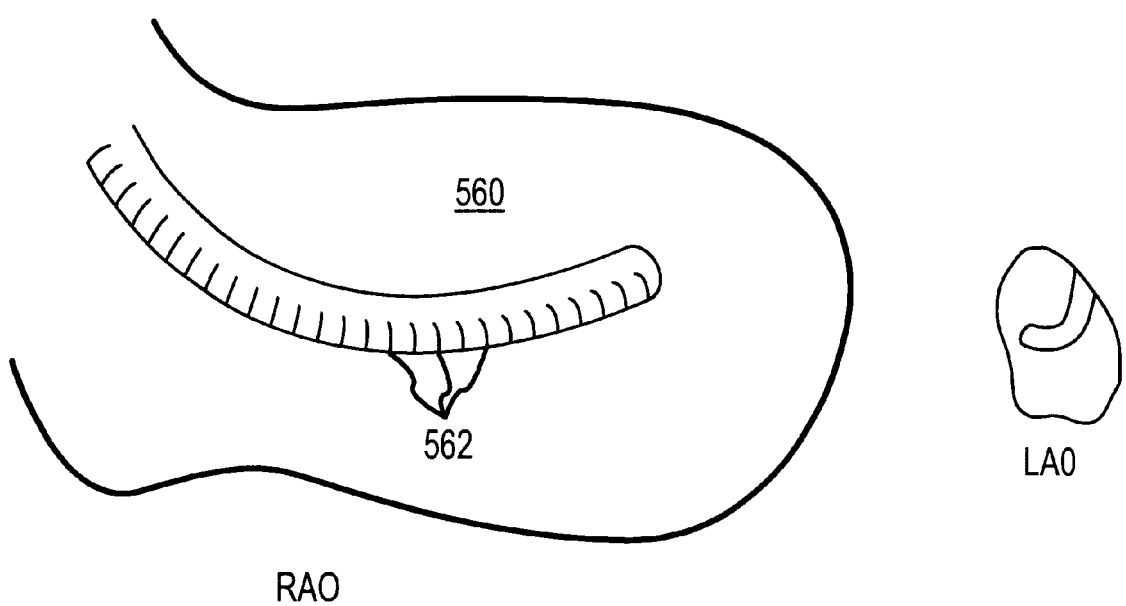
FIG. 5I is another representative RAO and LAO projection view of the distal end of an intraventricular catheter in the left ventricle with set of radially asymmetrically spaced radio opaque markers in reverse orientation as shown in FIG. 5H.

FIG. 5H is a representative RAO and LAO projection view of the distal end 560 of an intraventricular catheter in the left ventricle with a set of radially asymmetrically spaced radio opaque markers 562 of the present invention. FIG. 5I is another representative RAO and LAO projection view of the distal end 560 of an intraventricular catheter in the left ventricle with a set of radially asymmetrically spaced radio opaque markers 562 in reverse orientation as shown in FIG. 5H. Thus, it is apparent that markers 562 can be placed on only one side of the distal tip 560 of the catheter system. Thus, by placing radially asymmetrical striping on one half of the distal end 562 of a catheter, such as 90° to the direction of tip deflection, lateral and septal views can be distinguished. This is shown in each LAO projection of FIG. 5H and FIG. 5I.

Figure 6A:
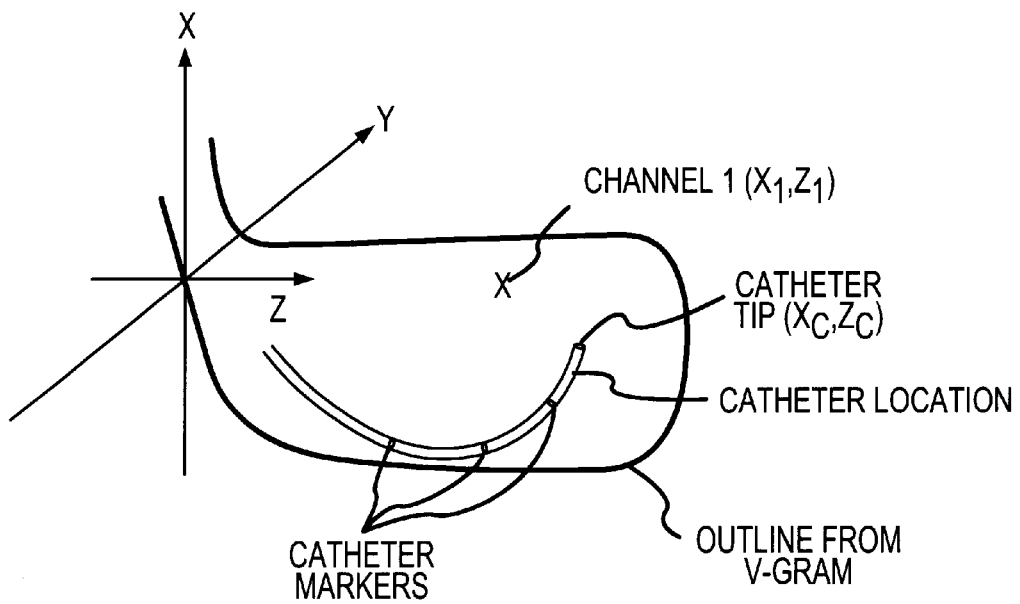
FIG. 6A is a representative RAO-30 projection view of an intraventricular catheter in the left ventricle within a 3-dimensional space defined by the coordinates of the X, Y, Z axis system of the present invention.
Figure 6B:
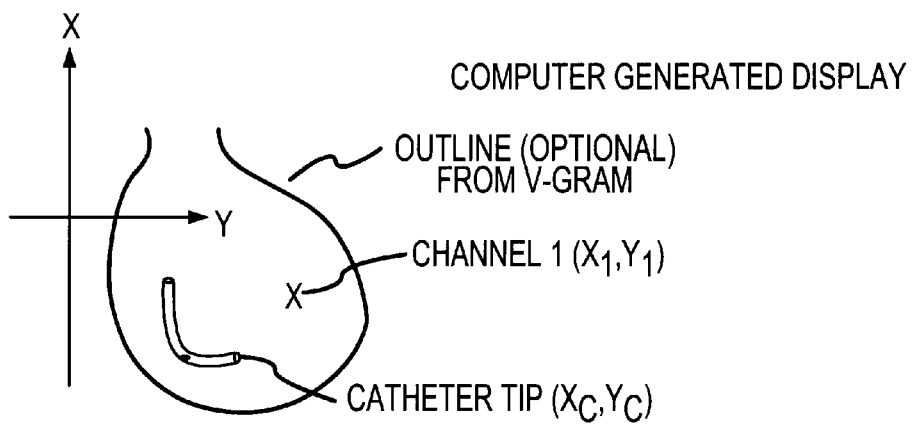
FIG. 6B is a representative LAO-60 projection view of an intraventricular catheter in the left ventricle in a plane defined by the coordinates of the X and Y axes of the present invention.

FIG. 6A is a representative RAO-30 projection view of an intraventricular catheter in the left ventricle within a 3-dimensional space defined by the coordinates of the X, Y, Z axis system of the present invention. FIG. 6B is a representative LAO-60 projection view of an intraventricular catheter in the left ventricle in a plane defined by the coordinates of the X and Y axes of the present invention.

Computer-based image analysis can track the location and dimensions of a cylindrical radio opaque marker located on the laser catheter and by comparing its measured dimensions obtained from analysis of the RAO projection, can determine the degree that the band is foreshortened. For example, if the tip were oriented directly toward the lateral or septal wall, the marker will have a completely circular appearance, and its dimensions will be equal in all directions. If the tip were oriented directly toward the anterior or inferior wall, the marker would have a "band" appearance, and its maximum and minimum dimensions would be at the highest possible ratio to each other. By tracking this ratio, the computer image analysis system can assess the rotational position and display this information on a "clock-face" display. This use of an embedded asymmetric shaft marker resolves the ambiguity regarding lateral/septal orientations.

The IAS will, optionally, replace the use of a manual input device to mark the location of the catheter tip as each treatment is performed by tracking the radiopaque marker included on the catheter tip. The IAS will track the tip location using edge and motion detection. As the catheter-based treatment is performed, the user will depress a "Location Mark" switch on the IAS console. Alternatively a footpedal can be used. A preferred embodiment provides for a signal to be sent from the treatment device, such as a laser, to indicate to the IAS that the current location of the catheter tip should be marked as a treatment location.

Opacification

Another fluoroscopic indication of foreshortening that could be used to assess rotational orientation is the degree of opacification. If the tip of the catheter shaft is constructed of a plastic that has been appropriately loaded with a radio opaque filler material, such as barium sulfate or bismuth subcarbonate, the tip will appear moderately opacified when viewed under a fluoroscope. The portion of the catheter shaft proximal to the distal tip will maintain this degree of opacification when viewed from an RAO projection regardless of the rotational orientation of the catheter. The portion of the catheter shaft distal to tip however, will vary in its degree of opacification, with its minimum opacification occurring when the catheter is oriented to either the anterior or inferior walls and its maximum opacification occurring when it is oriented to either the lateral or septal walls. Similarly, the length of this distal segment can be analyzed by a computer-based image analysis system to assess foreshortening and therefore rotational orientation.

Channel Mapping

Figure 7:
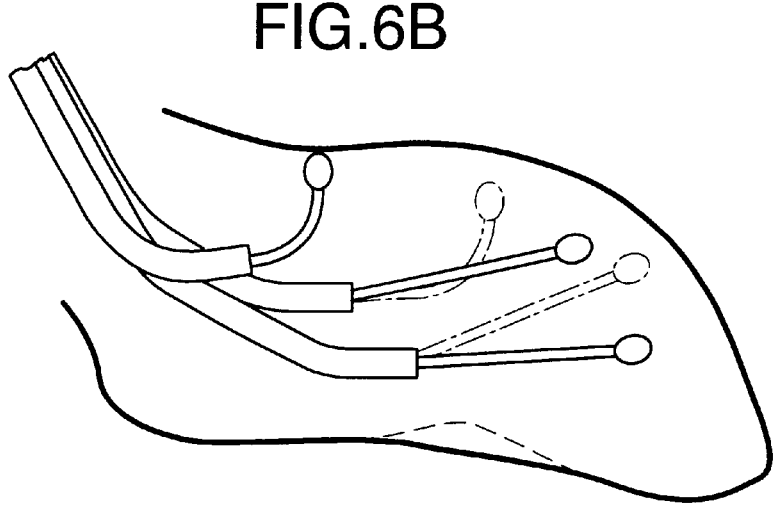
FIG. 7 is a representative RAO-30 projection view of the distal end tip of an intraventricular device directed perpendicularly towards internal surface areas of the left ventricle.

FIG. 7 is a representative RAO-30 projection view of the distal end tip of an intraventricular device directed perpendicularly towards internal surface areas of the left ventricle.

Figure 8:
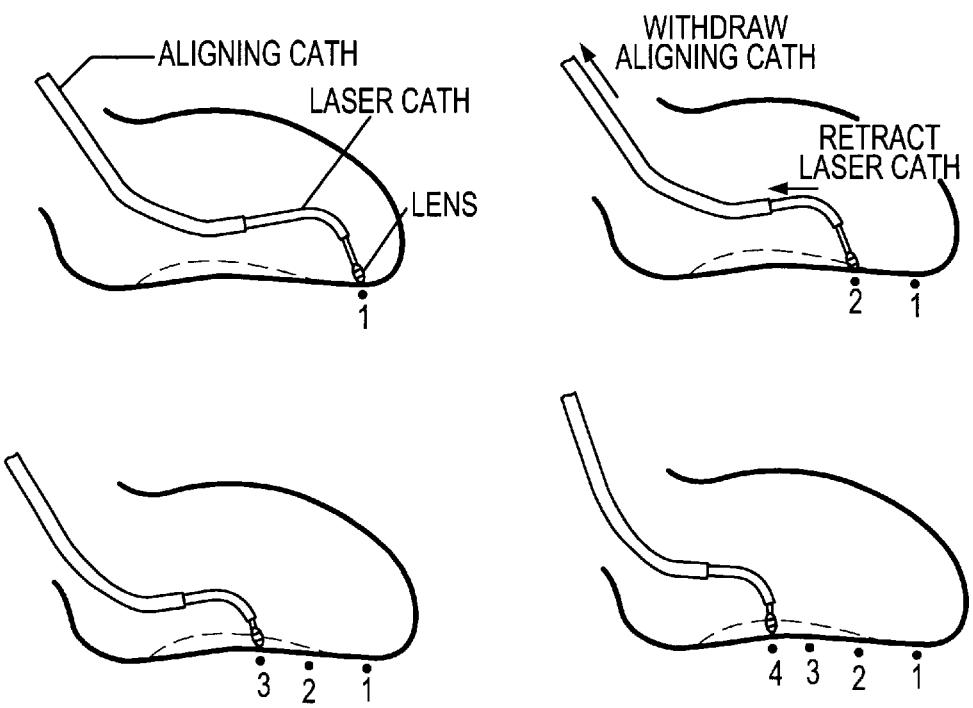
FIG. 8 is a representative RAO-30 projection view of a series of channels formed by the distal end tip of an intraventricular device directed perpendicularly towards internal surface areas of the left ventricle as the catheter tip is deflected and the energy delivery catheter is extended and retracted.

FIG. 8 is a representative RAO-30 projection view of a series of channels formed by the distal end tip of an intraventricular device directed perpendicularly towards internal surface areas of the left ventricle as the catheter tip is deflected and the energy delivery catheter is extended and retracted.

Figure 9:
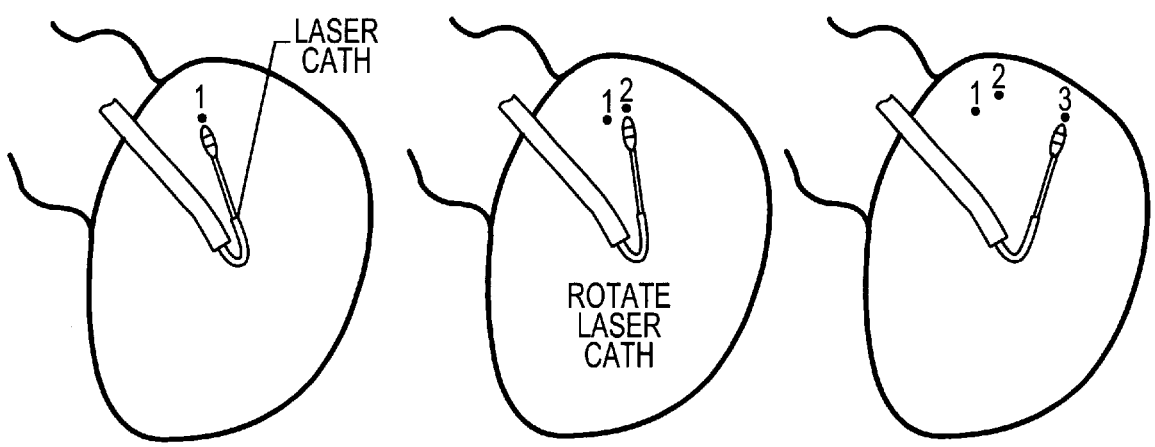
FIG. 9 is a representative LAO-60 projection view of a series of channels formed by the distal end tip of an intraventricular device directed perpendicularly towards internal surface areas of the left ventricle as the catheter system is rotated about its central, elongated axis and the energy delivery catheter is extended and retracted.

FIG. 9 is a representative LAO-60 projection view of a series of channels formed by the distal end tip of an intraventricular device directed perpendicularly towards internal surface areas of the left ventricle as the catheter system is rotated about its central, elongated axis and the energy delivery catheter is extended and retracted.

Once rotational orientation is known, a modified channel map technique is employed to record the location of previously formed channels and prevent the occurrence of "rechanneling." This map consists of the 2-D location of the lens marker recorded as each channel is created along with an associated rotational orientation value. Thus the "X-Y" values obtained from the RAO projection are augmented with the "Theta" value obtained through image analysis.

As the catheter is tracked in the ventricle by the image analysis system or computer 102, the location of a channel is marked either in two or three dimensions. Adding input from the laser, or other treatment device, to the computer allows for automatic marking of channels or treatment locations. This can be accomplished by adding a marker on the video display corresponding to the location of the catheter tip during the time which the treatment occurs. The location can be marked throughout the cardiac cycle to allow for the treatment location to properly track the changes throughout the cardiac cycle.

Markers are placed on the catheter to allow changes in the position in the catheter in the plane orthogonal to the fluoroscopic image to be detected and quantified by changes in shape in the marker. This data is displayed on one or two displays. The first display can be the fluoroscope display which shows real-time fluoroscopic images with computer generated information overlaid including outlines of the ventricle, catheter location, channel location and/or catheter orientation. For reference this data could be considered to describe locations on the X-Z plane.

A second display would be completely computer generated and would represent data in the Y-Z plane. The Z plane data would be taken directly from the fluoroscopic image and would correspond to the data in the X-Z plane display. The shape of the ventricle could be derived from the ventriculogram by collecting data from this plane during the ventriculogram. Alternatively either a default shape or no shape could be displayed. Catheter position and/or channel location could be displayed on both displays using the estimated X,Y,Z coordinates. Similarly, knowing the X,Y,Z coordinates of the channels and of the catheter tip, the distance from the catheter tip to the nearest channel can be calculated and displayed.

It will be understood that the use of radio opaque markers and digital signal processing techniques avoids the need for direct fluoroscopic imaging in more than a single projection. In other words, the fluoroscope can remain stationary throughout the procedure. Typically, a RAO-30 projection will be most useful. Out of plane shape and motion of the left ventricle as well as orientation and position of the catheter within the left ventricle are determined utilizing digital signal processing of radio opaque marker data. Furthermore, the use of an operator for manually marking heart and/or left ventricle outline, other physical structures, and channels or treatment mapping on a physical transparency over a fluoroscopic monitor can be replaced using the frame grabber, edge detection and character/image recognition algorithms described herein.

Input Signals

The live, single-plane, fluoroscopic image would be transferred to the image-analysis system or computer 102 as a standard NTSC composite video signal over a BNC cable. Appropriate modifications to allow use of other video formats, such as PAL, would also be included. Alternatively, a digital data stream of the live fluoroscopic image would be extracted from the catheter lab fluoroscope system and transferred to the image-analysis system 102. If required, ECG and respiration signals will be provided to the image-analysis system 102.

Image Recognition

The image-analysis system 102 would be capable of recognizing the location of the distal radio opaque marker and to update its 2D location within a fixed image field at an appropriate rate, perhaps 3 to 10 Hz. The image-analysis system 102 would be capable of recognizing the degree of "ellipticity" of the radio opaque marker and assigning some numerical value to this parameter, updated at the same rate as above. Since the marker is preferably a thin-walled, cylindrical gold band, its fluoroscopic appearance ranges from a perfect circle, when the longitudinal axis of the tip lies parallel to the tube-II axis, to a rectangular band, when the tip lies perpendicular to the tube-II axis. By displaying the current ellipticity value as the catheter system is navigated within the ventricle the user will be able to more completely determine catheter tip position and orientation using only an RAO-30 projection.

The ellipticity value will be a substitute for the direct determination of the rotational position of the laser catheter; such determination would require an LAO-60 view.

Analysis of Distal Tip Position

The combination of the 2-D marker position with the ellipticity value produces a 3-parameter description of the tip position which is almost unambiguous. The remaining ambiguity lies in the inability to distinguish between the tip oriented to, for example, the anteroseptal corner ("10 o'clock," when seen from an LAO-60) and the anterolateral corner ("2 o'clock"). Two methods are proposed to remove this ambiguity and thus provide a unique "3.5"-parameter description of any tip position:

An additional radio opaque marker would be placed on shaft of the laser catheter proximal to the distal end. This marker is wedge-shaped and its placement on the catheter is such that its fluoroscopic appearance is that of an "upward" pointing arrow when the tip of the laser catheter is oriented laterally ("3:00") and a "downward" pointing arrow when the tip of the laser catheter is oriented septally ("9:00"). The image-analysis system is capable of recognizing this asymmetric marker and uses its appearance to distinguish between tip positions that have equal ellipticities.

No additional markers are needed. Instead, the user would be required to depress an "L" (lateral) or "S" (septal) key during the course of the PMR procedure. The image-analysis system uses this input to distinguish between tip positions that have equal ellipticities. In order to provide this input without reference to an LAO-60 view, the user must consider rotational direction of the laser catheter following either anterior or inferior alignment.

Display

The image-analysis system would provide a display screen that showed the current 2D lens position and also indicated the calculated rotational position, for instance by displaying a simulated LAO-60 view on which a line representing the tip of the laser catheter is rotated. The display screen would also show a map of the location of all channel attempts. The user would provide a "channel-attempt here" input so that the image-analysis system could place a mark at that location. The channel mark would be placed in a consistent location with respect to both the cardiac and respiratory cycles. This would be accomplished by one of the following methods:

1. Triggering the signal placement to the ECG and respiration inputs.
2. Tracking the lens position for some minimum time to determine the extent of its excursion and then marking the location at a fixed proportion of this excursion.

Channel marks would be fixed on the display screen 112. In other words, it is not necessary to show channel locations in a continuously "animated" loop.

The image-analysis system should also provide a "channel duplication" function which determines whether or not the current lens location is identical to a previously marked channel (taking into account the excursion of the marked channel and of the current location). This determination may be either continuously displayed or available only when requested.

Image Generation

A computer with a frame grabber could be configured to capture video data going to a fluoroscope monitor 112. This video data can be further processed using image processing techniques to show additional information. This subsystem with a computer, frame grabber, with the fluoroscope connected will be referred to as the image computer 102.

Structural Locations

During a PMR procedure a ventriculogram is preformed in which radio opaque dye is injected into the ventricle. This creates an image on the fluoroscope to show the outline of the ventricle. The image computer can be designed with image processing algorithms to detect the transition from the dye-outlined ventricle and the other areas of the image. This allows the outline of the ventricle to be stored and displayed on the monitor during the procedure. Additionally, it is known that the size and shape of the ventricle changes with the cardiac cycle. Adding an input to the image computer which correlates to the cardiac cycle such as the ECG signal would allow the image computer to capture, store and register several images of the ventricle shape all corresponding to different, but known periods during the cardiac cycle. This also allows a monitor to be updated with the generated image one time per cardiac cycle, which allows the user to see changes (such as motion of the catheter) which do not have the additional motion of the cardiac cycle superimposed.

It is also known that during the respiratory cycle the heart moves relative to a fixed reference outside of the body such as the fluoroscope. The motion due to respiration can be tracked by monitoring the respiratory cycle. Alternatively, the image of the ventricle can be tracked relative to a reference point within the body if such reference point moves less relative to the heart than an external reference. This reference point can be a radio opaque marker placed within the anatomy using a reference catheter or a marker placed on the outside of the body such as on the chest or back. Alternatively, the image computer can use a reference point such as the ribs, wires from a previous sternotomy. The tracking of the image relative to a marker significantly reduces errors introduced due to changes in heart location due to respiration and/or patient movement.

Thickness Estimation

In addition to the ventriculogram, an angiogram can be performed by injecting radio opaque dye into the coronaries. Using image processing techniques, the angiogram could be used to estimate the outer surface of the ventricle, while the ventriculogram can be used to estimate the inner surface. If orthogonal data is collected (using either bi-plane fluoroscopy or a single plane device in two orthogonal positions) two complete surfaces with the myocardium thickness could be estimated. If single plane data is collected, then the myocardial thickness in that plane can be estimated.

Catheter Tracking

These markers could also be tailored to allow for optimal or easier tracking by an image processing system. For example, a series of 3 bands on the catheter or specialized shapes allow for easier identification and tracking by the image computer. Any method of marking the catheter in a manner in which the pattern is significantly different than naturally occurring patterns aids in tracking of the catheter.

Wall Contact Detection

Wall contact may be assessed based on changes in the fluoroscopic appearance of the catheter.

When using catheters with independently extendable contact elements, such as that described in Kesten et al., wall contact may be detected by the back-deflection that occurs in the portion of the delivery-catheter shaft proximal to the distal curve as the extendable tip of the device contacts the wall. A similar means can be employed when using deflectable-tip catheters, such as that described in Khairkahan et al. Wall contact can be detected by a change in motion of the distal catheter tip, typically to a reciprocating motion caused by the cardiac cycle of contraction and expansion. Detecting these changes can require training and experience as well as close attention to the fluoroscopic monitor.

Therefore, when the catheter is not in contact with the heart wall, the motion of the catheter will be independent of the patient's cardiac cycle. When the catheter is in contact with the heart wall, the motion of the catheter can be correlated with the cardiac cycle. Wall contact detection, therefore, is accomplished by correlating the motion of the catheter to the cardiac cycle. This is implemented by creating a correlation function between the amplitude of the catheter movement with the ECG signal. If the maximum amplitude of the correlation function exceeds a fixed threshold, then the wall contact indicator indicates contact.

Additionally, (as shown previously in FIG. 6A), a 3-dimensional image of the left ventricle can be generated using all of the 3-D data. This image such as a wire frame model could be displayed and allow the operator to rotate the image to allow visualization of the data, including total dynamic shape of the left ventricle corresponding with the entire cardiac cycle, planned treatment area and actual channel placement.

Figure 10A:
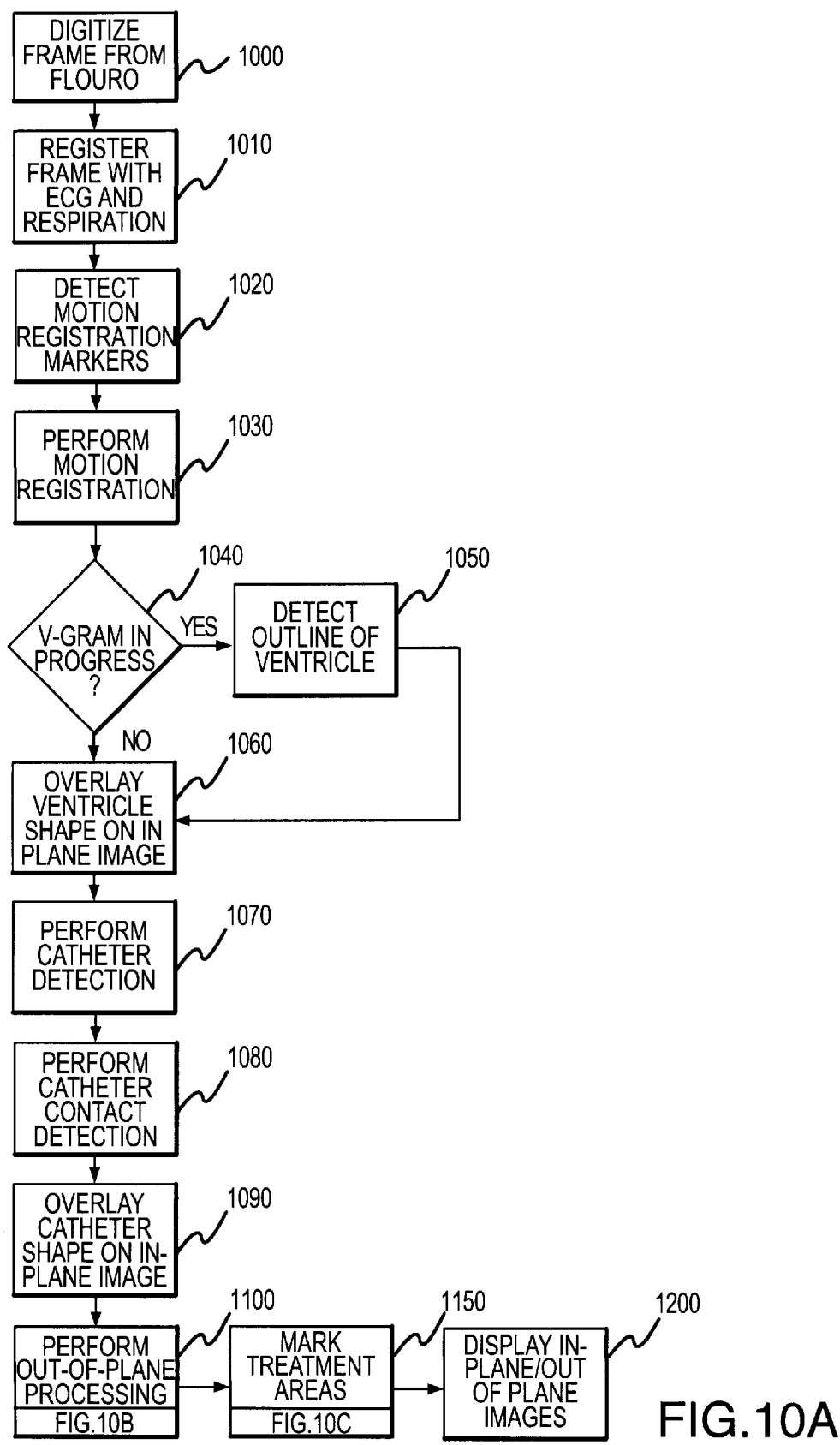
FIGS. 10A, 10B and 10C are a representative flowchart of a preferred embodiment of a method of PMR of the system of the present invention.
Figure 10B:
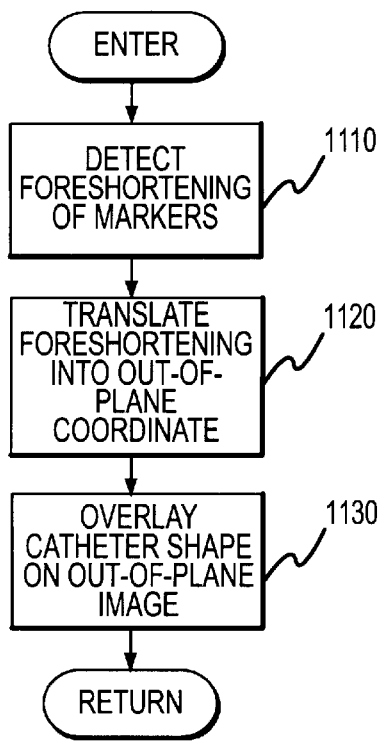
Figure 10C:
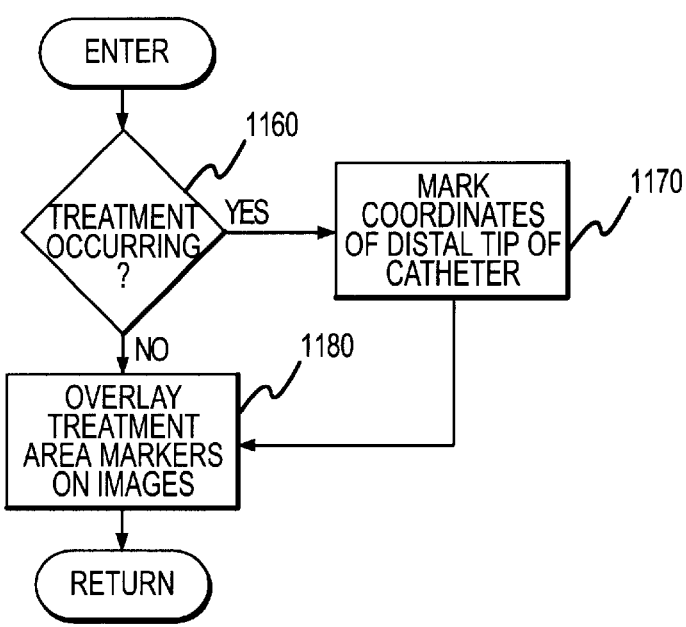

FIGS. 10A, 10B and 10C are a representative flowchart of a preferred embodiment of a method of PMR of the system of the present invention. Based on the foregoing, it will be understood that in an initial step 1000 in the flowchart relating to a preferred embodiment of the fluoroscopic tracking enhanced intraventricular catheter system of the present invention, individual frames of video data are captured via adapted "frame grabber" or data capture mechanism, including hardware, firmware and software, etc. It will be understood that typical fluoroscopy systems are adapted for providing video output. Other, more expensive systems provide digital video data output.

In a subsequent step 1010, the data from the frame captured in step 1000 is registered with respect to parameters including ECG and respiration signals generated by the patient. This registration step 1010 is a signal processing step in which the image is enhanced in any of various ways, including removal of noise, synchronization of the data stream with the other vital statistics of the patient, etc. In any event, this data is processed for producing enhanced imaging.

Detection of motion registration markers is performed in a step 1020. Typically, motion markers on the patient may include fluoroscopic markers placed on the patient at known positions, wire used in prior sternotomies, etc. A given marker can be ascertained or detected in step 1020 and will provide a characteristic digital pattern, based on any type of standard or custom character- or image-recognition system based on digital signal processing. Once the markers are detected, motion of the patient from an original position can be detected and the digital data corrected therefor. Thus, motion of the markers is registered in step 1030, and the position of the body can be known and recorded throughout the procedure.

In step 1040, the system determines when a ventriculogram is being performed. When a ventriculogram is in progress, the system will detect the outline of the ventricle in step 1050, with data collected for 2-dimensional imaging as well as for 3-dimensional imaging also. Once a ventriculogram has been performed, as shown in step 1060, the shape of the ventricle is overlaid on the fluoroscopic image, which can be either 2 or 3 dimensional.

At a certain point in the procedure 1070, the catheter is detected and the position projected on a visualization monitor. The data regarding the position of the catheter can also be stored. Thus, it will be understood by those skilled in the art that the precise location of the catheter within the left ventricle at all times can be determined and visualized, and data corresponding to the motion of the catheter throughout the procedure can be collected and stored as a historical archive of the catheter procedure.

As described, contact of the distal tip or other portion of the catheter can be determined in step 1080 by utilizing an algorithm or algorithms which compare the data generated by any of various fluoroscopic markers disposed on or within the catheter itself. As an example, when the data generated by the fluoroscopic image of a marker near the tip of the catheter indicates that the tip of the catheter is in motion, and when it is determined that the motion of the tip of the catheter has a unique correspondence with the cardiac cycle, it can be known when the tip of the catheter is in contact with a surface wall within the left ventricle. By analyzing the data, as in step 1080, confirmation of contact can be made, and the precise location within the left ventricle of contact between the tip of the catheter and the heart surface can also be known and recorded.

In a subsequent step 1090, the shape and position of the catheter is recorded and the data processed to superimpose the catheter on the in-plane image. As described above, the shape and position of the catheter in the in-plane image can be directly visualized via known fluoroscopic methods. However, as taught herein, the out of plane processing which is then performed on the catheter image in a subsequent step 1100 provides accurate information and data related to the position, shape and orientation of the catheter in planes other than that of the fluoroscope. In a preferred embodiment, the step 1100 of performing the out of plane processing consists of detection of the degree of foreshortening of the markers, step 1110. This is done, as described, by comparison of their shape (i.e. ellipticity), orientation, opacity, etc., and may include comparison against known or standardized shapes. With digital signal processing techniques, including edge detection and image/character recognition, the foreshortening determined in step 1110 can be used to determine the out of plane image properties of the catheter, step 1120, i.e., the out of plane coordinates. Finally, once the in plane and out of plane coordinates of the catheter are determined, the catheter can be superimposed on the out of plane image of the left ventricle, step 1130.

As shown, however, once the out of plane processing of the position and orientation of the catheter is performed in step 1100, the treatment areas are marked in step 1150. This step is accomplished by initially determining step 1160, whether or not treatment is to take place. If it is then a channel is to be formed. In that case, in step 1170, the coordinates of the distal tip of the catheter are marked and recorded. The coordinates of the distal tip of the catheter, obtained in step 1170, are then used as an overlay to indicate the points of treatment within the image of the ventricle, step 1180. This is also referred to, above, as channel marking or channel mapping. Using a 3-dimensional model, the spatial orientation of channels on the various surfaces of the left ventricle can be determined and visualized, step 1200.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A fluoroscopic tracking enhanced intraventricular catheter system for enhanced visualization of single-plane fluoroscopic images, the system comprising:

a fluoroscope for generating fluoroscopic image data;

a fluoroscopic image visualization monitor;

an intraventricular catheter having an elongated shaft, distal tip and a radiopaque portion adjacent the distal tip, the catheter adapted for delivery of energy to predetermined treatment areas on intraventricular surfaces; and an image analysis means, the image analysis means for receiving fluoroscopic image data from the fluoroscope and for determining physical parameters related to the left ventricle, for determining the relative position, orientation and motion of the catheter therewithin, and for determining the location and other parameters of treatment on intraventricular surfaces;

wherein the radiopaque portion comprises a circumferential radiopaque band such that when the distal tip of the catheter is oriented parallel with the plane of the image, the image of the radiopaque band appears as a rectangular stripe, and when the distal tip of the catheter is oriented perpendicular to the image plane, the image of the radiopaque band appears as a circular ring, and when the distal tip of the catheter is oriented at any predetermined angle other than parallel with or perpendicular to the image plane, the image of the radiopaque band appears to have a corresponding, predetermined ellipticity, the image analysis means capable of analyzing the image of the catheter and the radiopaque band, thereby determining the relative position, orientation and motion of the catheter.

2. The system of claim 1 in which the radiopaque portion comprises a polymeric material loaded with a radiopaque material.

3. A fluoroscopic tracking enhanced intraventricular catheter system for enhanced visualization of single-plane fluoroscopic images, the system comprising:

a fluoroscope for generating fluoroscopic image data;

a fluoroscopic image visualization monitor;

an intraventricular catheter having an elongated shaft, distal tip and a radiopaque portion adjacent the distal tip, the catheter adapted for delivery of energy to predetermined treatment areas on intraventricular surfaces; and an image analysis means, the image analysis means for receiving fluoroscopic image data from the fluoroscope and for determining physical parameters related to the left ventricle, for determining the relative position, orientation and motion of the catheter therewithin, and for determining the location and other parameters of treatment on intraventricular surfaces;

wherein the radiopaque portion comprises a plurality of circumferential radiopaque markings.

4. A fluoroscopic tracking enhanced intraventricular catheter system for enhanced visualization of single-plane fluoroscopic images, the system comprising:

a fluoroscope for generating fluoroscopic image data;

a fluoroscopic image visualization monitor;

an intraventricular catheter having an elongated shaft, distal tip and a radiopaque portion adjacent the distal tip, the catheter adapted for delivery of energy to predetermined treatment areas on intraventricular surfaces; and an image analysis means, the image analysis means for receiving fluoroscopic image data from the fluoroscope and for determining physical parameters related to the left ventricle, for determining the relative position, orientation and motion of the catheter therewithin, and for determining the location and other parameters of treatment on intraventricular surfaces;

wherein the radiopaque portion comprises an asymmetric radiopaque marker.

5. A method of performing an intraventricular procedure utilizing a fluoroscopic tracking enhanced intraventricular catheter system, the catheter of the catheter system having a generally elongated shape and a radiopaque portion adjacent the distal tip thereof, the method comprising the following steps:

generating digital data from a single-plane fluoroscopic image of the ventricle, thereby determining the shape of the left ventricle;

introducing the distal tip of the catheter into a ventricle;

detecting the radiopaque portion of the catheter in a single-plane fluoroscopic image, thereby determining the position of the distal tip of the catheter inside the ventricle; and performing out-of-plane processing of the radiopaque portion single-plane fluoroscopic image data, thereby determining the orientation of the distal tip of the catheter inside the ventricle.

6. The method of claim 5 further comprising the following step:

mapping the locations within the ventricle at which the intraventricular procedure was performed.

7. The method of claim 5 further comprising the following step:

enhancing the digital data from the single-plane fluoroscopic image by registration of the image with data input corresponding to the cardiac cycle of the patient.

8. The method of claim 5 further comprising the following step:

enhancing the digital data from the single-plane fluoroscopic image by registration of the image with data input corresponding to the respiratory cycle of the patient.

9. The method of claim 5 further comprising the following step:

enhancing the digital data from the single-plane fluoroscopic image by registration of the image with data input corresponding to physical movement of the patient.

10. The method of claim 5 further comprising the following step:

detecting contact between the distal tip of the catheter and an inner surface of the ventricle.

11. The method of claim 10 in which contact is determined based on fluoroscopic visualization of the relative motion between the distal tip of the catheter and an inner surface of the ventricle.

12. The method of claim 10 in which contact is determined by a positive correlation between the motion of the distal tip of the catheter and the cardiac cycle.

13. The method of claim 10 in which contact is determined by a predetermined periodic movement of the distal tip of the catheter.

14. The method of claim 5 further comprising the following step:

determining the orientation of the distal tip of catheter prior to performing the intraventricular procedure.

15. The method of claim 14 further comprising the following step:

determining the orientation of the distal tip of the catheter during performance of the intraventricular procedure.

16. The method of claim 14 further comprising the following step:

determining a map of the motion of the distal tip of the catheter throughout the performance of the intraventricular procedure.

17. The method of claim 14 further comprising the following step:

determining a map of treatment areas on the inner surfaces of the ventricle by the distal tip of the catheter throughout the performance of the intraventricular procedure.

18. The method of claim 5 in which the step of performing the out-of-plane processing determines the degree of foreshortening of the image of the catheter within the ventricle.

19. A method for performing an intracardiac catheter-based procedure using an enhanced fluoroscopic image, the method comprising the following steps:
   obtaining a fluoroscopic image of the catheter;
   enhancing the fluoroscopic image with an input device, wherein the fluoroscopic image is enhanced for showing the outline of the cardiac chamber being treated; and
   injecting radiopaque contrast agent into the chamber to be visualized.

20. The method of claim 19 in which the fluoroscopic image is enhanced for showing treatment sites within the cardiac chamber being treated, the method further comprising the step of marking the treatment sites as they are formed.

21. The method of claim 19 in which the fluoroscopic image is enhanced by detecting anatomical landmarks within the patient being treated, the method further comprising the step of using the anatomical landmarks as reference points for providing treatment.

22. The method of claim 19 in which the fluoroscopic image is enhanced by detecting fluoroscopically visible material within the patient being treated, the method further comprising the step of using the fluoroscopically visible material as reference points for providing treatment.

23. The method of claim 19 in which the intracardiac catheter-based procedure utilizes an image analysis computer, and the step of enhancing the fluoroscopic image includes the step of performing image analysis on the fluoroscopic image.

24. The method of claim 23 in which the image analysis step consists of performing edge detection.

25. The method of claim 23 in which the image analysis step consists of performing motion detection.

26. The method of claim 23 in which the image analysis step consists of tracking the location of the tip of the catheter.

27. The method of claim 23 in which the image analysis step consists of tracking the location of treatment performed by the catheter.

28. The method of claim 19 in which a cylindrical radiopaque tip marker is used to assess both the 2-dimensional location of the catheter within the fluoroscopic image as well as the rotational orientation of the catheter.

29. The method of claim 28 in which the shape of the radiopaque marker is detected.

30. The method of claim 29 in which cylindrical marker appears circular when the rotational orientation of the catheter is to target the lateral and septal regions.

31. The method of claim 29 in which cylindrical marker appears like a stripe when the rotational orientation of the catheter is to target the anterior and inferior regions.

32. The method of claim 19 in which the step of enhancing the fluoroscopic image includes the step of providing a "clockface" LAO projection in conjunction with an RAO projection of the fluoroscopic image.

33. The method of claim 32 in which the "clockface" LAO projection shows the anterior region from about 11 o'clock to about 2 o'clock, the lateral region from about 2 o'clock to about 5 o'clock, the inferior region from about 5 o'clock to about 8 o'clock, and the septal region from about 8 o'clock to about 11 o'clock.

34. The method of claim 19 in which the step of enhancing the fluoroscopic image of the catheter is performed by detecting an asymmetrical shaft marker mounted proximal to the distal tip of the catheter.

35. The method of claim 34 further comprising the step of determining the orientation of the asymmetrical shaft marker.

36. The method of claim 35 further comprising the step of determining the angular rotation and orientation of the catheter.

37. The method of claim 35 further comprising the step of distinguishing the lateral and the septal orientations.

38. The method of claim 19 further comprising the step of detecting a plurality of evenly-spaced radiopaque bands along the distal portion of a catheter with a deflectable tip.

39. The method of claim 38 further comprising the step of distinguishing changes in catheter rotation from changes in catheter deflection.

40. The method of claim 19 in which the step of enhancing the fluoroscopic image comprises cardiac gating.

41. The method of claim 19 in which the step of enhancing the fluoroscopic image comprises respiratory gating.

42. A method for performing an intracardiac catheter-based procedure using an enhanced fluoroscopic image, the method comprising the following steps:
   obtaining a fluoroscopic image of the catheter;
   enhancing the fluoroscopic image with an input device, wherein the fluoroscopic image is enhanced by detecting external radiopaque material applied to the patient being treated; and
   using the external radiopaque material as reference points for providing treatment.

43. The method of claim 42 in which the fluoroscopic image is formed using data obtained from at least two orthogonal projections of the chamber.

44. The method of claim 43 in which the orthogonal projections are about 90 degrees apart.

45. The method of claim 43 in which the orthogonal projections are about RAO-30 and about LAO-60.

46. The method of claim 42 in which the fluoroscopic image is obtained with a bi-plane fluoroscope, the method further comprising the step of enhancing the fluoroscopic image by superimposing on the image a map of the therapeutic treatment.

47. The method of claim 46 in which the bi-plane fluoroscopic image is a live image.

48. The method of claim 46 in which the bi-plane fluoroscopic image is a captured image.

49. The method of claim 46 in which the bi-plane fluoroscopic image is obtained from orthogonal projections.

50. The method of claim 46 in which the single-plane fluoroscopic image is a live image.

51. The method of claim 42 in which the fluoroscopic image is obtained with a single-plane fluoroscope, the method further comprising the step of enhancing the fluoroscopic image by superimposing on the image a map of the therapeutic treatment.

52. The method of claim 51 in which the single-plane fluoroscopic image is a captured image.

53. The method of claim 51 in which the single-plane fluoroscopic image is obtained from orthogonal projections.

54. The method of claim 53 in which the method further comprises the step of storing a portion of the image for future display.

55. The method of claim 54 in which the stored portion of the image is a still image.

56. The method of claim 54 in which the stored portion of the image is a video image.

* * * * *